United States Patent [19]

Archer

[11] 3,968,125

[45] July 6, 1976

[54] DIHYDROXYHEXAHYDRODIBENZO[b,d]-PYRANS

[75] Inventor: Robert A. Archer, Indianapolis, Ind.

[73] Assignee: Eli Lilly and Company, Indianapolis, Ind.

[22] Filed: Nov. 5, 1973

[21] Appl. No.: 413,010

[52] U.S. Cl. ............................ 260/345.3; 424/283; 260/340.9
[51] Int. Cl.[2] ............... C07D 311/78; C07D 311/76
[58] Field of Search ................................ 260/345.3

[56] References Cited
UNITED STATES PATENTS

| | | | |
|---|---|---|---|
| 3,507,885 | 4/1970 | Fahrenholtz | 260/345.3 |
| 3,636,058 | 1/1972 | Fahrenholtz | 260/345.3 X |
| 3,873,576 | 3/1975 | Petrzilka | 260/345.3 |

OTHER PUBLICATIONS

Farenholtz et al., J.A.C.S. 88 (1966) 2079–2080.
Farenholtz et al., J.A.C.S. 89, (1967), 5934–5941.

*Primary Examiner*—Howard T. Mars
*Attorney, Agent, or Firm*—James L. Rowe; Everet F. Smith

[57] ABSTRACT

1,9-Dihydroxy-3-alkyl-6a,7,8,9,10,10a-hexahydro-6H-dibenzo[b,d]pyrans, useful as hypotensive agents, as psychotropic drugs, particularly as anti-anxiety and/or antidepressant drugs, and as sedative and/or analgesic drugs.

5 Claims, No Drawings

DIHYDROXYHEXAHYDRODIBENZO[B,D]PYRANS

BACKGROUND OF THE INVENTION

1-Hydroxy-9-keto-3-alkyl-7,8,9,10-tetrahydro-6H-dibenzo[b,d]pyrans (preferably named as 1-hydroxy-3-alkyl-6,6a,7,8,10,10a-hexahydro-9H-dibenzo[b,d,]pyran-9-ones) were synthesized as intermediates by Fahrenholtz, Lurie and Kierstead, J. Am. Chem. Soc., 88, 2079 (1966), 89 5934 (1967) according to the following reaction procedure: a 5-alkyl resorcinol is reacted with diethyl α-acetylglutarate to form an ethyl 4-methyl-5-hydroxy-7-alkylcoumarin-3-propionate. Cyclization of this lactone ester with a metal hydride yields a tricyclic keto lactone of the following structure (I):

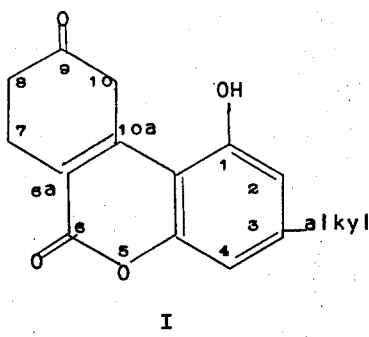

I

Protection of the 9-keto group by ketal formation followed by treatment of the ketal with a methyl Grignard Reagent and subsequent cyclization and removal of the ketal group yields a 1-hydroxy-3-alkyl-6,6-dimethyl-6,6a,7,8,-tetrahydro-9H-dibenzo[b,d,]pyran-9-one of Formula II below:

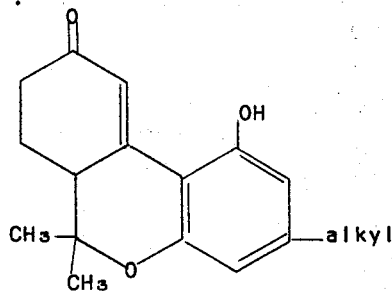

II

Reduction of the $\Delta^{10(10a)}$ double bond with lithium in liquid ammonia at −78°C. yields predominantly the trans ketone, dl-trans-(1-hydroxy-3-alkyl-6,6-dimethyl-6,6aβ, 7,8,10,10aα-hexahydro-9H-dibenzo[b,d]pyran-9-one) Formula III, along with minor quantities of the corresponding 6a,10a cis isomer.

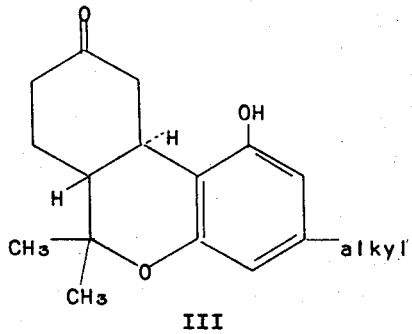

III

No pharmacological activity was reported for this compound and it was used only as an intermediate. Compounds according to Formula III can readily be transformed by treatment with a methyl Grignard Reagent to the corresponding 9-methyl-9-hydroxy compound, dehydration of which yields directly either a $\Delta^8$ or $\Delta^9$-tetrahydrocannabinol derivative, the latter being an active constituent of hashish. The Fahrenholtz et al synthesis is also described in U.S. Pat. No. 3,507,885 and in U.S. Pat. No. 3,636,058, a continuation-in-part of the previous patent. (In the Fahrenholtz et al patents, structure VI corresponds to Formula I above, structure VII to Formula II above, and structure III to Formula III above). Although apparently only a single compound of Formula III above was actually prepared by Fahrenholtz (the 3-n-pentyl derivative — see Example 8 of U.S. Pat. No. 3,636,058), a large number of alkyl substituted resorcinols are described, all of which can be used to synthesize other 3-alkyl derivatives of Formula III. Resorcinols named include 5-(1,2-dimethylheptyl)resorcinol, 5-(1-methyloctyl)resorcinol, 5-(1-methylhexyl)resorcinol, 5-(1,2-dimethylbutyl)-resorcinol, etc. A review article "Problems of Drug Dependence - Cannabis (Marijuana) Selected Bibliography (1950–1967) prepared by the Medical Literature Branch, Bureau of Medicine, FDA, Department of Health, Education and Welfare, *Addendum I, Substances Occurring Naturally in Marijuana*, etc., Isbel, (Washington, D.C., 1968)" and an article entitled *Recent Advances in the Chemistry of Hashish*, Mechoulam and Gaoni, *Fortschritte Der Chemie Organicher Naturstoffe*, 25, 175 (Springer, Wien, 1957) mention the Fahrenholtz, et al synthesis as well as other synthetic procedures for preparing active tetrahydrocannabinols; no pharmacological activity for compounds having a ketone ring group at 9 in the dibenzopyran ring system is recorded therein. 1,9-Dihydroxy-3-alkyl-6a,7,8,9,10,10a-hexahydro-6H-dibenzo[b,d]pyrans have not hitherto been prepared.

SUMMARY OF THE INVENTION

This invention provides 1,9-dihydroxy-3-alkyl-6a,7,8,9,10,10a-hexahydro-6H-dibenzo[b,d]pyrans of Formula IV:

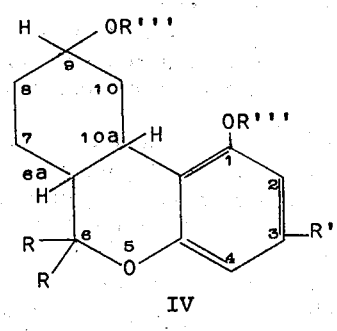

IV wherein R' is either $C_4$–$C_{10}$ normal alkyl or is

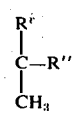

wherein R″ is $C_1$–$C_7$ alkyl or $C_2$–$C_7$ alkenyl, $R^v$ is H or methyl, each R‴ is individually hydrogen or $C_1$–$C_4$ alkanoyl, and wherein both R groups are the same and can be hydrogen or methyl.

The compounds of this invention are pharmacologically active. They manifest this activity in standard pharmacological tests as hypotensive agents, analgesics, sedatives, anti-anxiety agents and anti-depressants. A compound according to formula IV above is prepared in unit dosage form consisting of a pharmaceutical carrier and, as a therapeutic agent, from 0.001 to 25 mg. of a compound of Formula IV. The dosage form may be administered one to six times daily, yielding a daily dosage in the range 0.001 to 100 mgs. of a compound of structure IV with the preferred daily dosage being in the range 0.001–20 mg. Dosage forms thus prepared and employed in the therapeutic treatment of hypertension, anxiety and/or depression or to provide analgesia or sedation.

Illustrative of R′ in Formula IV when it is $C_4$–$C_{10}$ normal alkyl are n-butyl, n-pentyl, n-hexyl, n-heptyl, n-octyl, n-nonyl and n-decyl. Illustrative groups which R″ can represent in the grouping

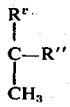

include
methyl, ethyl, n-propyl, isopropyl, sec-butyl, n-butyl, isobutyl, iso-amyl, t-amyl, n-amyl, 2-pentyl, 3-pentyl, 3-methyl-2-butyl, 2-hexyl, 1-hexyl, 3-hexyl, 4-methyl-1-pentyl, 3-methyl-1-pentyl, 3-methyl-2-pentyl, neopentyl, 3,3-dimethyl-1-butyl, 3,3-dimethyl-1-pentyl, 2-methyl-2-butenyl, 2-methyl-2-propenyl, allyl, methallyl, crotyl and the like groups. Thus groups illustrative of R′, when it is the above grouping, include the following: 1,2-dimethylheptyl, 1,1-dimethylheptyl, 1,2-dimethylhexyl, 1,1-dimethylpentyl, isopropyl, t-butyl, secbutyl, 1,1-dimethylpropyl, 1-methylbutyl, t-pentyl, 1-methyloctyl, 1-methylheptyl, 1-methylhexyl, 1,2-dimethyl-3-hexenyl, 1,1-dimethyl-2-heptenyl, 1-methyl-2-butenyl and the like. The term $C_1$–$C_4$ alkanoyl which R‴ can represent includes acetyl, propionyl, n-butyryl and isobutyryl.

The following dihydroxyhexahydrodibenzopyrans illustrate the scope of Formula IV above for compounds useful in the processes and compositions of this invention.

1-acetoxy-9-hydroxy-3-n-heptyl-6a,7,8,9,10,10a-hexahydro-6H-dibenzo[b,d]pyran;

1-hydroxy-9-propionoxy-3-(1′-methyl-2′-butenyl)-6,6-dimethyl-6a,7,8,9,10,10a-hexahydro-6H-dibenzo[b,d]pyran;

1,9-dipropionoxy-3-(1′-methylheptyl)-6,6-dimethyl-6a,7,8,9,10,10a-hexahydro-6H-dibenzo[b,d]pyran;

1,9-dihydroxy-3-(40 ,1′-dimethylheptyl)-6a,7,8,9,10,10a-hexahydro-6H-dibenzo[b,d,]pyran;

1-butyroxy-9-hydroxy-3-(1′, 2′-dimethylpentyl)-6,6-dimethyl-6a,7,8,9,10,10a-hexahydro-6H-dibenzo[b,d,]pyran;

1,9-dihydroxy-3-(1′, 1′-dimethyl-2-butenyl)-6a,7,8,9,10,10a-hexahydro-6H-dibenzo[b,d]pyran;

1,9-dihydroxy-3-n-butyl-6,6-dimethyl-6a,7,8,9,10,10a-hexahydro-6H-dibenzo[b,d]pyran;

1,9-dihydroxy-3-(1′,1′-dimethylhexyl)-6,6-dimethyl-6a,7,8,9,10,10a-hexahydro-6H-dibenzo[b,d,]pyran;

1,9-diacetoxy-3-n-pentyl-6a,7,8,9,10,10a-hexahydro-6H-dibenzo-[b,d]pyran;

1,9-dihydroxy-3-(1′-methyl-2′-butenyl)-6,6-dimethyl-6a,7,8,9,10,10a-hexahydro-6H-dibenzo[b,d]pyran;

1-propionoxy-9-hydroxy-3-(1′-methylheptyl)-6,6-dimethyl-6a,7,8,9,10,10a-hexahydro-6H-dibenzo[b,d]pyran;

1,9-dihydroxy-3-(1′,1′-dimethylhexyl)-6a,7,8,9,10,-10a-hexahydro-6H-dibenzo[b,d]pyran;

1n-butyroxy-9-hydroxy-3-(1′,1′-dimethylpentyl)-6,6-dimethyl-6a,7,8,9,10,10a-hexahydro-6H-dibenzo[b,d]pyran;

1,9-dihydroxy-3-(1,40 ,1′-dimethyl-2′-butenyl)-6,6-dimethyl-6a,7,8,9,10,10a-hexahydro-6H-dibenzo[b,d]pyran.

Compounds according to formula IV above contain asymmetric centers at 6a,9 and 10a. In addition, there may be asymmetric centers in the side-chain alkyl group as, for example, when R′ is 1,2-dimethylheptyl, two asymmetric centers are present in this side-chain. The Fahrenholtz synthetic procedure described above in which the double bond isomerizes from the $\Delta^{6a(10a)}$ position to the $\Delta^{10(10a)}$ position produces a racemate in which $C_{6a}$ is asymmetric, the hydrogen being either above or below the plane of the dibenzopyran fused-ring system. Hydrogenation of the $\Delta^{10(10a)}$ double bond with, for example, an active metal in liquid ammonia produces a second asymmetric center at $C_{10a}$, but the hydrogen which adds to this carbon under the hydrogenation or reduction conditions will usually take the more favorable trans configuration relative to the hydrogen at $C_{6a}$ with a lesser quantity of compound of the cis configuration being produced. Reduction of the ketone group at $C_9$ to give compounds according to formula IV above yields a mixture of isomers in which the hydroxyl group is in the axial ($9\alpha$) or equatorial ($9\beta$) configuration. Thus, synthesis of a compound in which the side chain contains no asymmetric centers, as for example 1,9-dihydroxy-3-(1,′,1′-dimethylheptyl)-6,6-dimethyl-6a, 7,8,9,10,10a-hexahydro-6H-dibenzo[b,d]pyran, will result in four racemates or racemic pairs to give a total of 8 diastereoisomers. Compounds such as 1,9-dihydroxy-3-(1′,2′-dimethylheptyl-6,6-dimethyl-6a,7,8,9,10,10a-hexahydro-6H-[b,d]pyran containing two asymmetric centers in the side chain will have a total of five asymmetric centers, those at 6a,9,10a and at $C_1$- and $C_2$- in the side chain, yielding altogether 32 possible isomers occuring as 16 racemates.

The compounds of this invention in which both R groups in the 6-position of Formula IV are methyl are prepared by reducing a ketone prepared by the procedure of Fahrenholtz et al referred to above. In the Farenholtz procedure, an alkyl resorcinol is condensed with a dialkyl α-acetoglutarate followed by cyclization with sodium hydride in DMSO to yield a compound according to Formula I above which, after initial formation and reaction with a Grignard Reagent followed by treatment with 6N acid, yields a 10,10a-dehydro-9H-dibenzo[b,d]pyran of Formula II above. Reduction of the $\Delta^{10(10a)}$ double bond then yields dimethyl ketones according to Formula III. Reduction of the ketone group with sodium borohydride or other metal hydride reducing agent yields a mixture of isomers at $C_9$. Since both isomers are pharmacologically active, the isomer mixture can be employed as such. If, however, it is desired to prepare either 9-hydroxy compound free from its 9-hydroxy isomer, special reaction conditions and/or reagents are employed. For example, reduction of a Farenholtz-type ketone with sodium borohydride at −78°C. yields a 9β-hydroxy derivative whereas reduction of the same ketone with potassium tri(sec-butyl)borohydride, also at −78°C. yields a 9α-hydroxy derivative.

Although the reduction of the ketone group has been illustrated above with reference to metal hydride reducing agents, as is well known in the art other reducing agents and systems are also available, such as catalytic hydrogenation. For example, not only will platinum and other noble metals reduce the ketone group of the formula III compounds to a secondary alcohol of formula IV, but will even reduce the conjugated ketone system of the compounds of formula II to the same secondary alcohol.

Compounds in which both R' groups attached to $C_6$ are hydrogen in Formula IV are prepared according to the following general procedure: The ketone group of a keto-lactone according to Formula I above is reacted with ethylene glycol to form the corresponding 9-ketal. Reduction of the ketal with sodium bismethoxyethoxyaluminum hydride in benzene yields a 2-(2'-hydroxymethyl-5'-ethylenedioxy-Δ¹-cyclohexenyl)-5-alkyl (or 5-alkenyl) resorcinol of formula V.

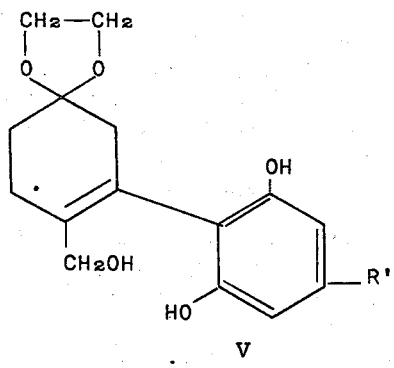

V

Cyclization of this resorcinol (V) with aluminum oxide in benzene yields a dekatalized derivative which, upon hydrogenation by the procedures of U.S. Pat. No. 3,507,885—either lithium, sodium, or potassium in liquid ammonia or hydrogenation over Raney nickel at a hydrogen pressure in the range 100–500 psi gives a dibenzo[b,d]pyran-9-one according to Formula III above in which both R groups attached to $C_6$ are hydrogen. Transformation of the 9-ketone group to a secondary alcohol or acylated alcohol is carried out as indicated above for the 6,6-dimethyl compounds.

Compounds in which both R''' groups in formula IV are the same and other than hydrogen are prepared by acylating a 1,9-dihydroxy compound. Compounds in which only the 9-hydroxyl is acylated are prepared by mild hydrolysis of the 1,9-diacyl derivative since the phenolic acyl group is preferentially hydrolyzed. On the other hand, compounds with an acyl group at $C_1$ and a hydroxyl at $C_9$ can be prepared by the borohydride reduction of a 1-acyl-9-keto derivative prepared by acylating a Farenholtz ketone. Compounds in which the acyl groups at 1 and 9 are different are prepared by acylating under carefully controlled conditions (so as to avoid umesterung) a 1-acyl-9-hydroxy or 1-hydroxy-9-acyl derivative.

The resorcinol starting materials useful in the Fahrenholtz synthesis such as n-hexyl resorcinol are readily available from the art. Resorcinols with a doubly branched alkyl group in the 5-position can be prepared by the procedure of Adams et al., J. Am. Chem. Soc., 70, 664 (1948). These α-branched 5-alkylresorcinols are in general produced by doubly alkylating a 3,5-dimethoxyphenylacetonitrile, converting the nitrile group to a ketone, reducing the ketone carbonyl to an alcohol, dehydrating the alcohol and then hydrogenating the resulting double bond. Demethylation then yields a 5-(1',1'-dimethylalkyl)resorcinol. Resorcinols having an alkyl side chain with an α-β-substitution pattern are in general prepared from 3,5-dimethoxybenzamide. Conversion of the benzamide to a ketone using the appropriate Grignard Reagent followed by the action of a methyl Grignard Reagent on the resulting ketone yields a tertiary carbinol. Dehydration of the carbinol produces an ethylenic compound which on hydrogenation yields a 3,5-dimethoxy-(α,β-substituted alkyl)benzene. This latter compound is readily demethylated to form the corresponding 5-(1'-methyl-2'-alkyl-substituted alkyl)resorcinol. 5-(α-substituted-alkenyl)resorcinols also useful as starting materials in the synthesis of dibenzopyranones are produced as intermediates in the above synthetic procedure. 5-alkyl resorcinols lacking an α-branch can be prepared by standard methods available in the art, including the reaction of a nitrile with a Grignard Reagent followed by reduction of the resulting carbonyl, dehydration of the thus formed benzylic alcohol and hyrogenation to yield an alkyl group, or by hydrogenolysis of a benzylic alcohol directly.

The synthetic procedure used for preparing compounds useful in the processes and compositions of this invention is illustrated by the following specific examples:

EXAMPLE I

Preparation of
dl-trans-1,9-dihydroxy-3-(1',1'-dimethylheptyl)-6aβ,7,8,9,10,10aα-hexahydro-6,6-dimethyl-6H-dibenzo[b,d]pyran;

To a stirred mixture of 2.15 g. of sodium borohydride in 75 ml. of absolute ethanol was added dropwise over a period of 1 hour a solution of 4.2 g. of dl-trans-1-hydroxy-3-(1',1'-dimethylheptyl)-6,6aβ,7,8,9,10,-10aα-hexahydro-6,6-dimethyl-9H-dibenzo[b,d]pyran-9-one in 100 ml. of absolute ethanol. After stirring at room temperature under an inert atmosphere for 16 hours, the mixture was slowly poured into 700 ml. of 0.1 N hydrochloric acid. Extraction with several portions of ether followed by washing of the combined ether extracts with saturated sodium chloride solution, drying the ether solution and evaporation of the ether under reduced pressure gave 4.1 g. (97%) of white solid containing a mixture of the axial (minor amount) and equatorial (major amount) alcohols of dl-trans-1,9-dihydroxy-3-(1',1'-dimethylheptyl)-6aβ,7,8,9,10,-10aα-hexahydro-6,6-dimethyl-6H-dibenzo[b,d]pyran having the following physical and chemical characteristics:

$R_f$=0.34 (minor isomer), 0.24 (major isomer) [silica gel, 5% MeOH:95% $CHCl_3$]; UV(EtOH)208, 230 and 280 mμ. (ε=47,200, 9,600 and 1,600); molecular ion, m/e=374.

Anal. Calc'd. for $C_{24}H_{38}O_3$: C, 76.96; H, 10.23; O, 12.81; Found: C, 76.72; H, 10.45; O, 12.78.

Other compounds prepared by the above procedure include the following:

dl-trans-1,9-dihydroxy-3-(1',2'-dimethylheptyl)-6a$\beta$,7,8,9,10,10a$\alpha$-hexahydro-6,6-dimethyl-6H-dibenzo[b,d]pyran having the following physical and chemical properties:

$R_f$=.30 (9$\alpha$–OH) and 0.23 (9$\beta$–OH) [silica gel, 5% MeOH; 95% CHCl$_3$]: UV(EtOH) 209, 230 and 280 mμ. (ε=43,200, 9,600 and 2,000): NMR (CDCl$_C$) δ6.20, 6.06(2S/2H/H$_2$ and H$_4$): δ4.30–3.0(m/2H/containing H$_{9\alpha\beta}$ H$_{10\alpha\beta}$ ) δ1.38, 1.03(2s/3H each/6$\beta$ and 6$\alpha$-CH$_3$): δ1.20(s/6H/$\alpha$-CH$_3$'s) and δ0.75ppm (3H/$\omega$CH$_3$); molecular ion, m/e=374

Anal. Calc'd. for $c_{24}H_{38}O_3$: C, 76.96; H, 10.23; O, 12.81; Found; C, 77.02; H, 10.40; O, 13.02.

dl-trans-1,9-dihydroxy-3-(n-pentyl)-6a$\beta$,7,8,9,10,-10a$\alpha$-hexahydro-6,6-dimethyl-6H-dibenzo[b,d]pyran having the following physical and chemical properties:

$R_f$=0.30(9$\alpha$ OH) and 0.23 (9$\beta$ OH) [silica gel, 5% MeOH: 95% CHCl$_3$]UV(EtOH) 209, 230 and 280 mμ. (ε=43,600, 10,400 and 2,000); NMR (CDCl$_3$-DMSO-d$_6$) δ6.16 (s/2H/H$_2$ and H$_4$); δ4.30–3.0(m/2H/containing H$_{9\alpha\beta}$ and H$_{10\alpha\beta}$ ); δ1.37 (s/3H/6$\beta$CH$_3$) δ1.03 (s/3H/6$\alpha$CH$_3$) and δ0.87 ppm (t/3H/$\omega$-CH$_3$); molecular ion, m/e=318

Anal. Calc'd. for $C_{20}H_{30}O_3$; C, 75.43; H, 9.50; O, 15.07; Found: C, 75.14; H, 9.78; O, 15.28.

dl-trans-1,9-dihydroxy-3-(t-butyl)-6a$\beta$,7,8,9,10,10a$\alpha$-hexahydro-6,6-dimethyl-6H-dibenzo[b,d]pyran having the following physical and chemical properties: $R_f$-0.28(9$\alpha$–OH) and 0.23(9$\beta$–OH) [silica gel. 5% MeOH: 95% CHCl$_3$]; UV(EtOH) 208, 230 and 275 mμ. (ε=43,600, 9,600 and 1,600); NMR (DCDl$_3$-DMSO-D$_6$) δ6.43/6.34 (2d/J=2cps/2H/H$_2$ and H$_4$); δ4.20–2.80 (m/2H/includes H$_{9\alpha\beta}$ and H$_{10\alpha\beta}$ ); δ1.37/1.05 (2s/3H each/6$\alpha$and 6$\beta$-CH$_3$); and δ1.25 ppm (s/9H/t-butyl group); molecular ion, m/e=304.

Anal. Calc'd. for $C_{19}H_{28}O_3$: C, 74.96; H, 9.27; O, 15.77; Found: C, 75.26; H, 9.47; O, 15.72.

EXAMPLE II

Preparation of
dl-cis-1,9-dihydroxy-3-(1',1'-dimethylheptyl)-6a$\beta$,7,8,9,10,10a$\beta$-hexahydro-6,6-dimethyl-6H-dibenzo[b,d]pyran To a mixture of 510 mg. of sodium borohydride in 30 ml. of ethanol was added in dropwise fashion a solution of 1.0 g. of dl-cis-1-hydroxy-3-(1',1'-dimethylheptyl)-6,6a$\beta$,7,8,10,10a$\beta$-hexahydro-6,6-methyl-9H-dibenzo[b,d]pyran-9-one in 30 ml. of ethanol. After stirring at room temperature under an inert atmosphere for 16 hours, the reaction mixture was poured into 200 ml. of 0.1 N. hydrochloric acid. Ether was added, and the layers were separated. The ether layer was washed with saturated sodium chloride solution, dried, and the ether evaporated under reduced pressure to give 1.0 g. (98%) of a white solid containing a mixture of the 9$\beta$-hydroxy and 9$\alpha$-hydroxy isomers of dl-cis-1,9-dihydroxy-3-(1',1'-dimethylheptyl)-6a$\beta$,7,8,9,10,10a$\beta$-hexahydro-6,6-dimethyl-6H-dibenzo[b,d]pyran having the following physical and chemical properties: UV (EtOH) 208, 230 and 273 mμ. (ε=42,400, 9,600 and 1,600): NMR (CDCl$_3$) δ6.34/6.26 (2d/J=2cps/H$_2$ and H$_4$); δ4.20–2.80 (m/2H/includes H$_{9\alpha\beta}$ and H$_{10\alpha\beta}$ ); δ1.17 (s/6H/$\alpha$CH$_3$'s) and δ0.83 ppm (t/3H/$\omega$-CH$_3$). molecular ion, m/e=374.

Anal. Calc'd for $C_{24}H_{38}O_3$: C, 76.96; H, 10.23; O, 12,81; Found: C, 76.73; H, 10.41; O, 12.60.

EXAMPLE III

Preparation of
dl-trans-1,9$\beta$-dihydroxy-3-(1',1'-dimethylheptyl)-6a$\beta$,7,8,9,10,10a$\alpha$-hexahydro-6,6-dimethyl-6H-dibenzo[b,d]pyran To a mixture of 1.02 g. of sodium borohydride in 30 ml. of ethanol at $-78°C$. was added in dropwise fashion a solution of 2.0 g. of dl-trans-1-hydroxy-3-(1',1'-dimethylheptyl)-6,6a$\beta$,7,8,9,10,10a$\alpha$-hexahydro-6,6-dimethyl-9H-dibenzo[b,d]pyran-9-one in 30 ml. of ethanol. stirring of the mixture was continued at $-78°C$. for 1 hour after the addition had been completed. Then 350 ml. of 0.1 N hydrochloric acid was added dropwise and the mixture extracted with several portions of ether. The ether extracts were combined. The combined extracts were washed with a saturated aqueous sodium chloride solution, dried, and the ether evaporated therefrom under reduced pressure to give 1.95 g. (97%) of a white solid, consisting of dl-trans--1,9$\beta$-dihydroxy-3-(1',1'-dimethylheptyl)-6a$\beta$,7,8,9,10,10a$\alpha$-hexahydro-6,6-dimethyl-6H-dibenzo[b,d]pyran having the following physical and chemical characteristics: NMR (CDCL$_3$) δ6.34/6.19(2d/J=2cps/2H/H$_2$ and H$_4$); δ4.04–3.67 (m/1H/H$_9\alpha$); δ3.53(brd/J=13cps/H$_{10\alpha}$ ) δ1.37/1.05 (2s/ each 3 H/6$\beta$ and 6$\alpha$-CH$_3$); δ1.18(S/6H/$\alpha$CH$_3$) and δ0.83 ppm (t/3H/$\alpha$-CH$_3$).

EXAMPLE IV

Preparation of dl-trans-1,9$\alpha$-dihydroxy-3-(1',1'-dimethylheptyl) 6a$\beta$, 7,8,9,10,10a$\alpha$-hexahydro-6,6-dimethyl-6H-dibenzo[b,d]pyran To 21 ml. of a 0.5 molar solution of potassium tri-(sec.-butyl)borohydride in tetrahydrofuran at $-78°C$. was added dropwise with stirring under an inert atmosphere a solution of 2.0 g. of dl-trans-1-hydroxy-3-(1',-1'-dimethylheptyl)-6,6a$\beta$,7,8,10,10a$\alpha$-hexahydro-6,6-dimethyl-9H-dibenzo[b,d]pyran-9-one in 20 ml. of tetrahydrofuran. After stirring at $-78°C$. for one hour, 50 ml. of water were added in dropwise fashion followed by 50 ml. of 2 N sodium hydroxide and 25 ml. of 30% aqueous hydrogen peroxide. The resulting mixture was extracted with several portions of ether. The ether extracts were combined; the combined extracts washed with water and dried; and the ether evaporated therefrom under reduced pressure to give 1.91 g. (95%) of a white solid; dl-trans-1,9$\alpha$-dihydroxy-3-(1',1'-dimethylheptyl)-6a$\beta$,7,8,9,10,10a$\alpha$-hexahydro-6,6-dimethyl-6H-dibenzo[b,d]pyran having the following physical and chemical characteristics: NMR(CDCL$_3$) δ6.36/6.28(2d/J=2cps/2H/H$_2$ and H$_4$): δ4.28(brs/1H/H$_{9\beta}$ ); δ3.22(brd)/J=14cps/1H/H$_{10\alpha}$ ) δ1.36/1.03 (2s/3H each 6$\beta$ and 6$\alpha$ CH$_3$); δ1.18(s/6h/$\alpha$ CH$_3$'s) and δ0.83 ppm (t/3h/$\omega$-CH$_3$).

The synthesis of the ketonic starting materials useful in the above examples is illustrated by the following preparations;

PREPARATION 1.

Preparation of
1-hydroxy-3-(1′,1′-dimethylheptyl)-6,6-dimethyl-6,6a,7,8,10,10a-hexahydro-9H-dibenzo[b,d]pyran-9-one.

A mixture containing 114 g. of 5-(1′,1′-dimethylheptyl) resorcinol, 112 g. of diethyl 2-acetylglutarate and 74 g. of phosphorous oxychloride was stirred at ambient temperature for about ten days. The reaction mixture was then dissolved in ethyl acetate and the ethyl acetate layer washed several times with an equal volume of water until the water wash was neutral to litmus. The organic layer was separated and dried, and the solvent removed by evaporation in vacuo. The residue, comprising ethyl 7-(1′,1′-dimethylheptyl)-5-hydroxy-4-methyl-2-oxy-2H-1-benzopyran-3-propioniate formed in the above reaction, was purified by chromatography over 2 kg. of neutral alumina using chloroform as the eluant. 142 g. of purified product thus obtained, were dissolved in 300 mll. of DMSO (dimethylsulfoxide), and the solution added in dropwise fashion to a suspension of 33.6 g. of sodium hydride in 100 ml. of DMSO. After the addition had been completed, the reaction mixture was allowed to stand at ambient temperature overnight. Excess sodium hydride present was decomposed by the dropwise addition of ethanol. The reaction mixture was next carefully poured over a mixture of ice and 12 N aqueous hydrochloric acid. A solid resulted comprising 3-(1′,1′-dimethylheptyl)-7,10-dihydro-1-hydroxy-6H-dibenzo[b,d]pyran-6,9(8H)-dione, which was collected by filtration. The solid filter cake was dissolved in methyl ethyl ketone and the resulting solution washed with 5 percent aqueous sodium bicarbonate followed by saturated aqueous sodium chloride. The organic layer was dried, and the solvent removed by evaporation in vacuo. Trituration of the crude residue with anhydrous ether followed by filtration (the filtrate being discarded) yielded about 92.6 g. of a light yellow solid. 3-(1′,1′-Dimethylheptyl)-7,10-dihydro-1-hydroxy-6H-dibenzo[b,d]pyran-6,9(8H)-dione thus obtained was used in its semi-purified state. A solution of 2.3 g. of the above product in 125 ml. of benzene also containing 2.5 ml. of ethylene glycol and 5 mg. of p-toulenesulfonic acid was heated overnight under reflux using a water collector. After cooling, the reaction mixture was poured into 5 percent aqueous sodium bicarbonate. The organic layer was separated, washed with water and then dried. Removal of the organic solvent in vacuo yielded 2.5 g. of 3-(1′,-1′-dimethylheptyl)-7,8-dihydro-1-hydroxyspiro[9H-dibenzo-[b,d]pyran-9,2′-[1,3]-dioxolan]-6(10H)-one. This product was also used without purification.

A solution of the product in 50 ml. of anhydrous ether was added dropwise to 46 ml. of a 2.8 M methyl Grignard Reagent in anhydrous ether. After the addition had been completed, the reaction mixture was refluxed overnight, cooled, and then carefully poured into an ice and 6N aqueous hydrochloric acid mixture. Evaporation of the ether by heating on a steam bath yielded a light yellow precipitate which was collected by filtration. The solid material was washed several times with ether to give 1.64 g. of a light yellow solid comprising dl-3-(1′,1′-dimethylheptyl) 6,6a,7,8-tetrahydro-1-hydroxy-6,6-dimethyl-9H-dibenzo[b,d]-pyran-9-one; MP = 194°–6°C.

Rf=0.26 (silica gel, 20% ethylacetate:benzene): UV-(ethanol) $\lambda_{max}$ 207/230/323 m$\mu$ ($\epsilon$=25,600/13,200/23,200); IR(Chloroform) 6.1 $\mu$(C=O): NMR (CDCL$_3$) $\delta$7.4 (d/J=2 cps/1H/H$_{10}$), $\delta$6.46/6.26(2d/J=2 cps/2H/H$_2$ and H$_4$), $\delta$1.21(s/6H/gem dimethyl at C-1′) and $\delta$9.83 ppm (t/3H/$\alpha$-methyl); molecular ion; m/e= 370.

A solution of 1.5 g. of dl-3-(1′,1′-dimethylheptyl)-6,6a,7,8-tetrahydro-1-hydroxy-6,6-dimethyl-9H-dibenzo[b,d]-pyran-9-one in 50 ml. of anhydrous tetrahydrofuran (THF) was added dropwise to a solution of lithium metal in liquid ammonia at −80°C. Excess lithium metal was added in chunks to the solution as the blue color, indicating free dissolved lithium, disappeared. After the addition was complete, ammonium chloride was added to react with any excess lithium metal still present. The mixture was then allowed to warm to room temperature in a nitrogen atmosphere during which process the ammonia evaporated. The reaction mixture was then acidified with 1N aqueous hydrochloric acid, and the organic constituents extracted with ethyl acetate. The ethyl acetate extracts were combined, washed with water and dried. Evaporation of the ethyl acetate under reduced pressure yielded 1.4 g. of crude dl-trans-3-(1′,1′-dimethylheptyl)-6,6-*hexahydro*-1-hydroxy-6,6-dimethyl-9H-dibenzo[b,d]pyran-9-one. The crude product was chromatographed over 50 g. of silica gel from benzene solution and the desired product was eluted in 20 ml. fractions with a benzene eluant containing 2 percent ethyl acetate. Fractions 200–240 contained 808 mg. of a white crystalline solid comprising purified dl-trans-3-(1′,1′-dimethylheptyl)-6,6a$\beta$,7,8,10,10$\alpha$-hexahydro-1-hydroxy-6,6-dimethyl-9H-dibenzo[b,d]pyran-9-one. The purified compound melted at 159°–160°C. after recrystallization from an ethyl acetate-hexane solvent mixture. R$_f$=.45 (silica gel, 20% ethyl acetate benzene).

UV(ethanol) $\lambda$max 207/280$\mu$ ($\epsilon$=47,000/250); IR(CHCl$_3$) 5.85 $\mu$(C=O); NMR (CDCL$_3$) $\delta$7.75(s/1H/exchanges with D$_2$O), $\delta$6.36/6.34 (2d/J=2 cps/2H/H$_2$ and H$_4$), $\delta$4.15(d broad/J=14,3 cps/1H/H$_{10}$ ), $\delta$3.08–0.7 (multiplet/32H), especially $\delta$1.47/1.13 (2s/each 3H/6$\alpha$ and 6$\beta$ CH$_3$), $\delta$1.21 (s/6H/gemdimethyl at C-1′) and $\delta$0.83 ppm (t/3H/$\omega$-methyl); molecular ion, m/e 372.

Anal. Calcd. for C$_{24}$H$_{36}$O$_3$: C, 77.38; H, 9.74; O, 12,88. Found: C, 77.59; H, 9.68; O, 12.99.

dl-cis-3-(1′,1′-dimethylheptyl)-6,6a$\beta$,7,8,10,10a$\beta$-hexahydro-1-hydroxy-6,6-dimethyl-9H-dibenzo[b,d]pyran-9-one was prepared by further elution of the above chromatographic column with benzene containing 5 percent ethylacetate. 140 mg of a white crystalline solid consisting of dl-cis-3-(1′,1′ -dimethylheptyl)-6,6a-7,8,10,10a-hexahydro-1-hydroxy-6,6-dimethyl-9H-dibenzo[b,d]pyran-9-one having the following physical and chemical characteristics: m.p. = 151°–153°; R$_f$ .38(Silica Gel, 20% EtOAc-benzene); NMR (CDCl$_3$) $\delta$6.98(s/1H/exchanges with D$_2$O), $\delta$6.36(s broad/2H/H$_2$ and H$_4$), $\delta$1.40, 1.35(2s/each 3H/6$\beta$ and 6$\alpha$ CH$_3$), $\delta$1.20 (s/6H/gem dimethyl at C-1′) and $\delta$0.83 ppm (t/3H/$\omega$-methyl); molecular ion, m/e 372.

Anal. Calcd. for C$_{24}$H$_{36}$O$_3$: C, 77.38; H, 9.74; O, 12,88 Found: C, 77.61; H, 10.00; O, 12.57.

Other compounds preparable by the above procedure include:

dl-trans-3-(1′,2′-dimethylheptyl)-6,6a$\beta$,7,8,10,10a$\alpha$-hexahydro-1-hydroxy-6,6-dimethyl-9H-dibenzo[b,d]- pyran-9-one having the following physical and chemical characteristics: m.p. 119°–120°; $R_f$=0.68 (silica gel, 20% ethylacetate:benzene); UV($C_2H_5OH$) λmax 208/280mμ (ε=48,400/800); IR (CHCl$_3$) 5.85μ (C=O); NMR CDCl$_3$) δ6.30 (brs/2H/aromatics); δ4.23(d broad/J=14.0, 3.0 cps/1H/$H_{10\alpha}$ );.δ1.50/1.15 (2s/each 3H/6α and 6β CH$_3$) and δ0.82 ppm(t/3Hω-methyl); molecular ion, m/e=372.

Anal. Calcd. for $C_{24}H_{36}O_3$: C, 77.38; H, 9.74; O, 12.88. Found: C, 77.67; H, 9.98; O, 13.00.

dl-trans-3-n-heptyl-6,6aβ,7,8,10,10αaβ, 7, 8, -hexahydro-1-hydroxy-6,6-dimethyl-9H-dibenzo[b,d]pryan-9-one having the following physical and chemical characteristics: m.p. 116°–117°; $R_f$32 0.38 (Silica gel, 20% ethyl acetate:benzene); UV($C_2H_5OH$) λmax 208.280mμ (ε=12,000/600); IR (CHCl$_3$) 5.87 μ (C=O); NMR (CDCl$_3$ δ7.95 (s/1H/exchanges with $D_2O$), δ6.30(s broad/2H/$H_2$ and $H_4$); δ4.22 (broad d/J = 14.0, 3.0/1H/$H_{10\alpha}$ ), δ1.30/1.12(2s/each 3H/6α and 6βCH$_3$) and δ0.87 ppm (t/3H/ω-methyl): molecular ion, m/e = 344.

Anal. Calcd. for $C_{22}H_{32}O_3$: C, 76.70; H, 9.36; O, 13.93. Found: C, 76.80; H, 9.12; O, 13.68.

dl-trans-1-hydroxy-3-(1'-methylheptyl)-6,6-dimethyl-6,6aβ,7,8,1,10aα-hexahydro-9H-dibenzo[b,d]pyran-9-one with these characteristics: m.p. 137°–138° $R_f$ 0.36 (Silica gel, 20% ethylacetate:benzene); UV-(EtOH) 208/280 mμ (ε=48,800/400); IR(CHCl$_3$) 5.86 μ (C=O); NMR(CDCl$_3$) δ7.8(s/1H/exchanges with $D_2O$), δ6.32(2H/$H_2$ and $H_4$), δ4.20 (d broad/J=14/3 cps/1H/$H_{10}$ ), δ1.48/1.13(2s/each 3H/6α and 6β CH$_3$), δ1.23 (s/6H/gem dimethyl at C-1') and δ0.83ppm (t/3H/ω-methyl); high resolution mass spec confirms MW = 358 and empirical formula $C_{23}H_{34}O_3$.

Other compounds preparable by the above procedure and useful in the processes of this invention include:

dl-trans-1-hydroxy-3-(1',1'-dimethylpentyl)-6,6-dimethyl-6,6aβ,7,8,10,10aα-hexahydro-9H-dibenzo[b,d]pyran-9-one dl-trans-1-hydroxy-3-(1',1'-dimethylpropyl)-6,6-dimethyl-6,6aβ,7,8,10,10aα-hexahydro-9H-dibenzo[b,d]pyran-9-one.

dl-trans-1-hydroxy-3-(1',1'-dimethyloctyl)-6,6-dimethyl-6,6aβ,7,8,10,10aα-hexahydro-9H-dibenzo[b,d]pyran-9-one.

The 1-acetoxy-9-keto derivatives according to the Formula III in which the R''' group at $C_1$ is $C_1$–$C_4$ lower alkanoyl are prepared by reacting a compound in which R''' at $C_1$ is hydrogen with a lower alkanoyl chloride or anhydride.

PREPARATION 2

Preparation of dl-trans-1-acetoxy-3-(1',1', -dimethylheptyl) 6,6-dimethyl-6,6aβ, 7,8,10,10,aα-hexahydro-9H-dibenzo]b,d]pyran-9-one:

A mixture of 500 mg. dl-trans-1-hydroxy-3-(1',1'-dimethylheptyl)-6,6-dimethyl-6,6aβ, 7,8,10,10aα-hexahydro-9H-dibenzo[b,d]pyran-9-one, 5 ml of acetic anhydride, and 5 ml. of pyridine was stirred under an inert atmosphere for 16 hours. The mixture was then poured onto ice and extracted with ethyl acetate. The ethyl acetate extract was washed with 1 N HCl and saturated sodium chloride solution, dried over anhydrous sodium sulfate and evaporated in vacuo to give 450 mg. of dl-trans-1-acetoxy-3-(1',1'-dimethylheptyl)-6,6-dimethyl-6,6aβ,7,8,10,10aα-hexahydro-9H-dibenzo[b,d]pyran-9-one as a viscous oil: $R_f$=0.33(Silica gel, 10% Ethyl acetate:benzene): IR (CHCl$_3$) 5.62, 5.80, and 8.28 μ; molecular ion at m/e 414.

As previously mentioned, compounds represented by formula IV above are useful in the treatment of hypertension or anxiety and/or depression in mammals as well as having the ability to provide sedation and/or analgesia also in mammals. They manifest these activities in standard laboratory tests; for example, dl-trans-1,9-dihydroxy-3-(1',1'-dimethylheptyl)-6,6-dimethyl-6aβ, 7,8,9,10,10aα-hexahydro-6H-dibenzo[b,d]pyran is an extremely potent hypotensive agent, with an ability to lower blood pressure in normotensive rats, rabbits, dogs or monkeys at dosages in the range of 1–2 mcg/kg of mammaliam weight by the iv route or in the range 16–32 mcg/kg of mammaliam weight orally and in genetically hypertensive rats at an oral dosage of 600 mcg per kg. To date, refractoriness to the continued administration of the compound has not developed. At some what higher doses, the same compound is a potent inhibitor of muricide in rats (minimum effective dose = 1.2 mg/kg when administered by mouth). The muricidal rat assay is one in which compounds having clinical utility as anti-depressants or appetite suppressants in mammals show activity. The same compound demonstrates excellent activity in taming septal-lesioned rats, having a minimum effective dose in this test of less than 5.0 mg/kg when administered orally. This test is a valuable test for detecting tranquilizer (anti-anxiety) activity of the type exhibited by diazepam and chlordiazepoxide. Food intake of these septallesion rats is not reduced except at doses greater than 5 mg/kg by the oral route. Compounds represented by Formula IV above, and useful in the processes of this invention, therefore have an advantage shown in the above two tests in that the effects in both the septal-lesioned rats and muricidal rats are seen at doses well below those at which appetite suppression takes place.

Compounds represented by Formula IV also show activity in the mouse-writhing test, a standard test for analgesic action. In particular, dl-trans-1,9-dihydroxy-3-(1',1'-dimethylheptyl)-6,6-dimethyl-,6aβ,7,8,9,10,1042 aα-hexahydro-6H-dibenzo[b,d]pyran at an oral dose level of 1.25 mg/kg gave a 79 percent inhibition of writhing at 180 min. In the rat tail jerk test, another standard laboratory test for analgesic action, oral doses from 0.1 to 5 mg/kg of rats weight of the same drug all elevate reaction times, which elevation is evidence of analgesic action. At higher dose levels, the compound manifested a sedative action in both mice and dogs.

Other compounds which show excellent activity in the above tests and are therefore potent hypotensive agents, anti-anxiety and/or anti-depressant drugs, analgesics and sedatives include dl-trans-1,9-dihydroxy-3-(1',1'-dimethylheptyl)-6,6-dimethyl-6aβ, 7,8,9,10,10aα-hexahydro-6H-dibenzo[b,d]pyran, dl-cis-1,9-dihydroxy-3-(1',1'-dimethylheptyl)-6,6-dimethyl-6aβ, 7,8,9,10,10aβ-hexahydro-6H-dibenzo[b,d]pyran, dl-trans-1,9-dihydroxy-3-(t-butyl)-6,6-dimethyl-6aβ,7,8,9,10,10aα-hexahydro16H-dibenzo[b,d]pyran and dl-trans-1,9-dihydroxy(n-pentyl)-6,6-dimethyl-6aβ, 7,8,9,10,10aα-hexahydro-6H-dibenzo[b,d]pyran.

Compounds represented by Formula IV above can be administered to mammals suffering from hypertension, from mental depression or who are extremely disturbed and anxious or who are in pain or in need of sedation, by either the oral or parenteral route, the oral route being preferred. The compounds are relatively insoluble and in preparing any pharmaceutical form containing them it is desirable that the compound be in a finely divided state such as that obtainable after rapid evaporation of a solution of the drug. In addition, aqueous suspensions of the drug should be used as soon as possible after being prepared, and the suspension concentrate should be maintained in the dry state until use.

An aqueous suspension of a drug represented by Formula IV is prepared as follows: An acetone solution containing 2 parts of weight of, for example, 1-9-hydroxy-3-(1',1'-dimethylheptyl)-6,6-dimethyl-6a, 7,8,9,10,10a-hexahydro-6H-dibenzo[b,d] pryan is mixed with 1 part by weight of aqueous polyoxyethylenesorbitan monooleate. The solution is placed in a glass ampoule, and the actone evaporated in vacuo. Just before use, 100 parts by weight of water are added giving a final drug concentration of 2 mg/ml.

Capsules containing drug according to formula IV above suitable for use in the processes of this invention can be prepared as follows: 0.1 part by weight of drug (obtained by adding an ethanol solution thereof rapidly to a large volume of water and then collecting the precipitate) is mixed with 9.9 parts of starch and the mixture loaded into empty telescoping gelatin capsules such that each capsules contains 1 mg of drug and 99 mg. of starch. Alternatively, a mixture containing 1 parts of drug from acetone solution, 0.1 part of polyoxyethylenesorbitan monooleate or similar suitable surfactant and 98.9 parts of starch are thoroughly mixed and placed in empty telescoping gelatin capsules such that each capsule will contain 1 mg. of drug. Solutions of compounds according to the above formula for use in oral administration can be prepared in any desired strength in polyethyleneglycol 300 (N.F.).

As will be understood by those versed in the art, it is possible to vary the amount of drug in each of the above dosage forms so that unit dosage will contain from 0.001 mg. to 25 mg. of drug with final daily dosages of from 0.001 mg. to 100 mg./patient.

I claim;
1. A compound of the formula

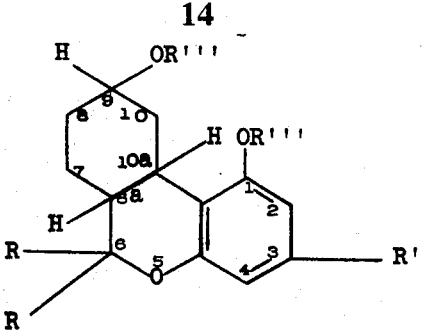

wherein R' is

wherein R'' is $C_1$–$C_7$ alkyl, $R^v$ is H or methyl, each R''' is individually hydrogen or $C_1$–$C_4$ alkanoyl, and wherein both R's are the same and can be hydrogen or methyl.

2. A compound according to claim 1, said compound being dl-trans-1,9-dihydroxy-3-(1',1'-dimethylheptyl)-6aβ, 7,8,9,10,10aα-hexahydro-6,6-dimethyl-6H-dibenzo[b,d]pyran 3. A compound according to claim 1, said compound being dl-trans-1,9-dihydroxy-3-(1',2'-dimethylheptyl)-6aβ, 7,8,9,10,10aα-hexahydro-6,6-dimethyl-6H-dibenzo[b,d]pyran 4. A compound according to claim 1, said compound being dl-trans-1,9-dihydroxy-3-(t-butyl)-6aβ, 7,8,9,10,10aα-hexahydro-6,6-dimethyl-6H-dibenzo[b,d]pyran 5. A compound according to claim 1, said compound being dl-cis-1,9-dihydroxy-3-(1',1'-dimethylheptyl1-6aβ, 7,8,9,10,10aβ-hexahydro-6,6-dimethyl-6H-dibenzo[b,d]pyran

* * * * *

UNITED STATES PATENT OFFICE
CERTIFICATE OF CORRECTION

Patent No. 3,968,125        Dated July 6, 1976

Inventor(s) Robert A. Archer

It is certified that error appears in the above-identified patent and that said Letters Patent are hereby corrected as shown below:

Column 3, line 60, "(40 ,1'-" should read --(1',1'- --.

Column 4, line 15, "(1,40 ,1'" should read --(1',1'--.

Column 5, line 51, "100-500" should read --100-5000--.

Column 7, line 39, "(DCDl₃" should read --CDCl₃--.

Column 10, line 25, "6,6-hexahydro-" should read --6,6aβ, 7,8,10,10aα-hexahydro--.

Column 10, line 33, "10α-hexahydro" should read --10aα-hexahydro--.

Column 10, line 42, "cps/1H/H₁₀ )" should read --cps/1H/H₁₀α)--.

Column 11, line 11, "10αaβ, 7, 8, hexahydro" should read -- 10aα-hexahydro--.

UNITED STATES PATENT OFFICE
CERTIFICATE OF CORRECTION

Patent No. 3,968,125          Dated July 6, 1976

Inventor(s) Robert A. Archer

It is certified that error appears in the above-identified patent and that said Letters Patent are hereby corrected as shown below:

Column 11, line 14, "$R_f 32$" should read --$R_f=0.38$--.

Column 11, line 25, "7,8,1,10a$\alpha$" should read --7,8,10,10a$\alpha$--.

Column 11, line 31, "1H/H$_{10}$)" should read --1H/H$_{10\alpha}$)--.

Column 12, line 45, "9,10,10$\alpha$2" should read --9,10,10--.

Signed and Sealed this nineteenth Day of July 1977

[SEAL]

Attest:

RUTH C. MASON
*Attesting Officer*

C. MARSHALL DANN
*Commissioner of Patents and Trademarks*